US00PP14921P2

(12) United States Plant Patent
Utecht

(10) Patent No.: US PP14,921 P2
(45) Date of Patent: Jun. 15, 2004

(54) GERANIUM PLANT NAMED 'FISROSALM'

(50) Latin Name: *Pelargonium zonale L'Héritier*
Varietal Denomination: Fisrosalm

(75) Inventor: Angelika Utecht, Montabaur (DE)

(73) Assignee: Florfis AG, Binningen (CH)

( * ) Notice: Subject to any disclaimer, the term of this patent is extended or adjusted under 35 U.S.C. 154(b) by 0 days.

(21) Appl. No.: 10/715,537

(22) Filed: Nov. 19, 2003

(30) Foreign Application Priority Data

Dec. 23, 2002 (CA) ..... PBR 02-3404

(51) Int. Cl.[7] ..... A01H 5/00

(52) U.S. Cl. ..... Plt./330

(58) Field of Search ..... Plt./330

*Primary Examiner*—Kent Bell
(74) *Attorney, Agent, or Firm*—Foley & Lardner LLP

(57) ABSTRACT

A new and distinct cultivar of geranium plant named 'Fisrosalm', particularly characterized by the combined features of rose red, round, cup-shaped, semi-double flowers, medium green foliage with distinct zonation, vigorous growth, tall and wide plant habit, and mid spring flowering response.

1 Drawing Sheet

Genus and species of the invention: Hybrid *Pelargonium zonale* L'Héritier.
Variety denomination: 'Fisrosalm'.

BACKGROUND OF THE INVENTION

The present invention comprises a new and distinct cultivar of geranium, botanically known as *Pelargonium zonale,* and hereinafter referred to by the cultivar named 'Fisrosalm'.

'Fisrosalm' is a product of a planned breeding program which had the objective of creating new zonal geranium cultivars with cultivars with semi-double flowers, relatively vigorous, but well-branched growth habit, good outdoor performance, and in various flower colors.

'Fisrosalm' originated from a hybridization made by the inventor, Angelika Utecht, in a controlled breeding program in Hillscheid, Germany, in 1997. The female parent was an unpatented hybrid seedling, no. 94-1112-2, having light pale pink and white semi-double flowers, medium-green foliage with relatively strong zonation, and moderately compact growth. The male parent of 'Fisrosalm' was the unpatented hybrid seedling no. 96-1059-3, with single-type, dark-pink flowers with red eyes on petals, large inflorescences, dark-green leaves without zonation, and medium sized plant habit.

'Fisrosalm' was selected as one flowering plant within the progeny of the stated cross by Angelika Utecht in 1998, in a controlled environment in Moncarapacho, Portugal.

The first act of asexual reproduction of 'Fisrosalm' was accomplished when vegetative cuttings were taken from the initial selection in the fall of 1998, in a controlled environment in Moncarapacho, Portugal, by, or under the supervision of, Angelika Utecht.

Horticultural examination of plants grown from cuttings of the plant initiated in May 1999 in Hillscheid, Federal Republic of Germany, and continuing thereafter, has demonstrated that the combination of characteristics as herein disclosed for 'Fisrosalm' are firmly fixed and are retained through successive generations of asexual reproduction.

BRIEF SUMMARY OF THE INVENTION

'Fisrosalm' has not been observed under all possible environmental conditions. The phenotype may vary significantly with variations in environment such as temperature, light intensity and day length. The following observations, measurements, and comparisons describe plants grown in Hillscheid, Germany, under greenhouse conditions which approximate those generally used in commercial practice.

The following traits have been repeatedly observed and are determined to be basic characteristics of 'Fisrosalm' in combination distinguish this geranium as a new and distinct cultivar:

1. Brilliant rose-red, semi-double flowers;
2. Medium to large inflorescences high above the foliage;
3. Medium-green foliage with distinct zonation;
4. Vigorous growth, tall, and very well-branched plant habit; and
5. Mid-spring flowering response, and floriferous throughout summer.

Of the many commercial cultivars known to the present inventor, the most similar in comparison to 'Fisrosalm' is the variety 'Fistwi' (U.S. Plant Pat. No. 13,190).

In comparison to 'Fistwi', 'Fisrosalm' has slightly less distinct foliage zonation. Furthermore, inflorescences of 'Fisrosalm' are somewhat smaller and have reddish-brown pedicels, while pedicels of 'Fistwi' are usually green. Additionally, plant habit of 'Fisrosalm' is generally wider.

BRIEF DESCRIPTION OF THE DRAWING

The accompanying photographic drawing shows typical flower and foliage characteristics of 'Fisrosalm' with colors being as true as possible with an illustration of this type. The photographic drawing shows a flowering potted plant of 'Fisrosalm'.

DETAILED BOTANICAL DESCRIPTION

The measurements were taken in Langley, British Columbia, Canada, in late July, 2003, 17 weeks after planting of rooted cuttings. The plants were growing in 20-cm pots, they had not been pinched.

In the following description color references are made to The Royal Horticultural Society Colour Chart. The color values were determined indoors from plants growing in a green-house in July 2003 in Langley, British Columbia, Canada.

INFLORESCENCE

Umbel:

*Shape.*—Semi-spherical.

*Average diameter.*—112 mm.

*Average depth.*—60 mm.

*Peduncle length.*—186 mm.

*Peduncle color.*—Light green, RHS 143 B, outdoors a slight tinge of reddish-brown may occur, approximately RHS 179 A.

*Pedicel.*—27 mm in length.

*Pedicel color.*—Reddish, RHS 179 A.

*Total number of flowers and buds per umbel.*—About 30–40.

Corolla:

*Average diameter.*—45 mm.

*Form.*—Semi-double-type.

*Shape.*—Round, open, flat cup-shape.

*Number of petals.*—7–9.

*Shape of petals.*—Obovate, base attenuate, upper end is rounded, margin is entire.

*Size of petals.*—Upper petals: 24–26 mm long, 18–20 mm wide; lower petals: 22–24 mm long, 19–21 mm wide.

*Color (general tonality from a distance of three meters)*.—Rose-red, occasionally with a slight bluish overtone.

*Color of upper petals.*—RHS 52 A, base of upper petals: salmon, RHS 50 B.

*Markings of upper petals.*—Absent.

*Color of lower petals.*—Between RHS 52 A and RHS 57 A.

*Markings of lower petals.*—Absent.

*Color of lower surface of petals.*—Between RHS 52 B to RHS 54 B.

*Color of sepals.*—Outer surface: light green, RHS 144 A; at the base: RHS 179 B; inner surface: light green, RHS 144 B.

*Number of sepals.*—5.

*Shape of sepals.*—Linear to lanceolate, acute tip, sessile (base), surface with weak pubescence, margin entire.

*Size of sepals.*—10–12 mm long, 4 mm wide for the largest upper sepal, 2–3 mm in width for the other sepals.

Bud: (just prior to petals unfolding).

*Shape.*—Elliptical.

*Color of sepals.*—Light green, RHS 143 C.

*Color of petals.*—RHS 45 B.

*Length.*—17 mm.

*Width.*—13 mm.

Reproductive organs:

*Androecium.*—5–7 fertile anthers, plenty pollen, yellow-orange, RHS 26 A, filaments white, RHS 155 D, to light-pink, RHS 52 D.

*Gynoecium.*—One pistil, whitish style, RHS 155 D to RHS 65 D, stigma 5–6 lobed, reddish, RHS 52 A.

*Fertility/seed set.*—Occasionally, weak. Fruit: Oblong, about 6 mm wide, rostrum (beak) 38–42 mm long. Seed: Oblong, 4–5 mm long, brown, RHS 177 B.

Spring flowering response period: In Hillscheid, Germany, in 2002 plants had on average 0.5 flowers opened 8 weeks after planting of rooted cuttings.

Outdoor flower production: Continuously and rich flowering, the flower count in 2002, in Hillscheid, Germany, indicated about 2–3 inflorescence per plant in mid May.

Durability: Good stability of flower color, relatively good rain resistance.

Lastingness of the individual flower: About 8 days at 18° C.

Fragrance: None

PLANT

Foliage:

*Shape.*—Kidney-shaped, with cordate base, with the gap between the lowest lobes open, apex rounded with weak lobes.

*Margin.*—Bi-crenated.

*Texture.*—Upper surface smooth, dull.

*Size of leaf.*—9.8 cm wide, 5.8 cm long.

*Color of upper surface.*—Medium green, approximately RHS 137 B.

*Color of zonation.*—Brown, about RHS 166 A, weak to medium distinctness.

*Color of lower surface.*—RHS 137 D.

*Petioles.*—Approximately 6–9 cm long, 3–3.5 cm diameter, light green in color, approximately RHS 143 C.

General appearance and form:

*Stem color.*—Light green, RHS 143 B.

*Internode length.*—20–40 mm.

*Branching pattern.*—5–7 branches.

*Size of plants.*—47 cm tall, 51 cm wide (17-week-old plants, as described, measured from the top of the soil (base of the main stem) to the surface of the foliage canopy, without inflorescences).

I claim:

1. A new and distinct cultivar of geranium plant named 'Fisrosalm', as described and illustrated herein.

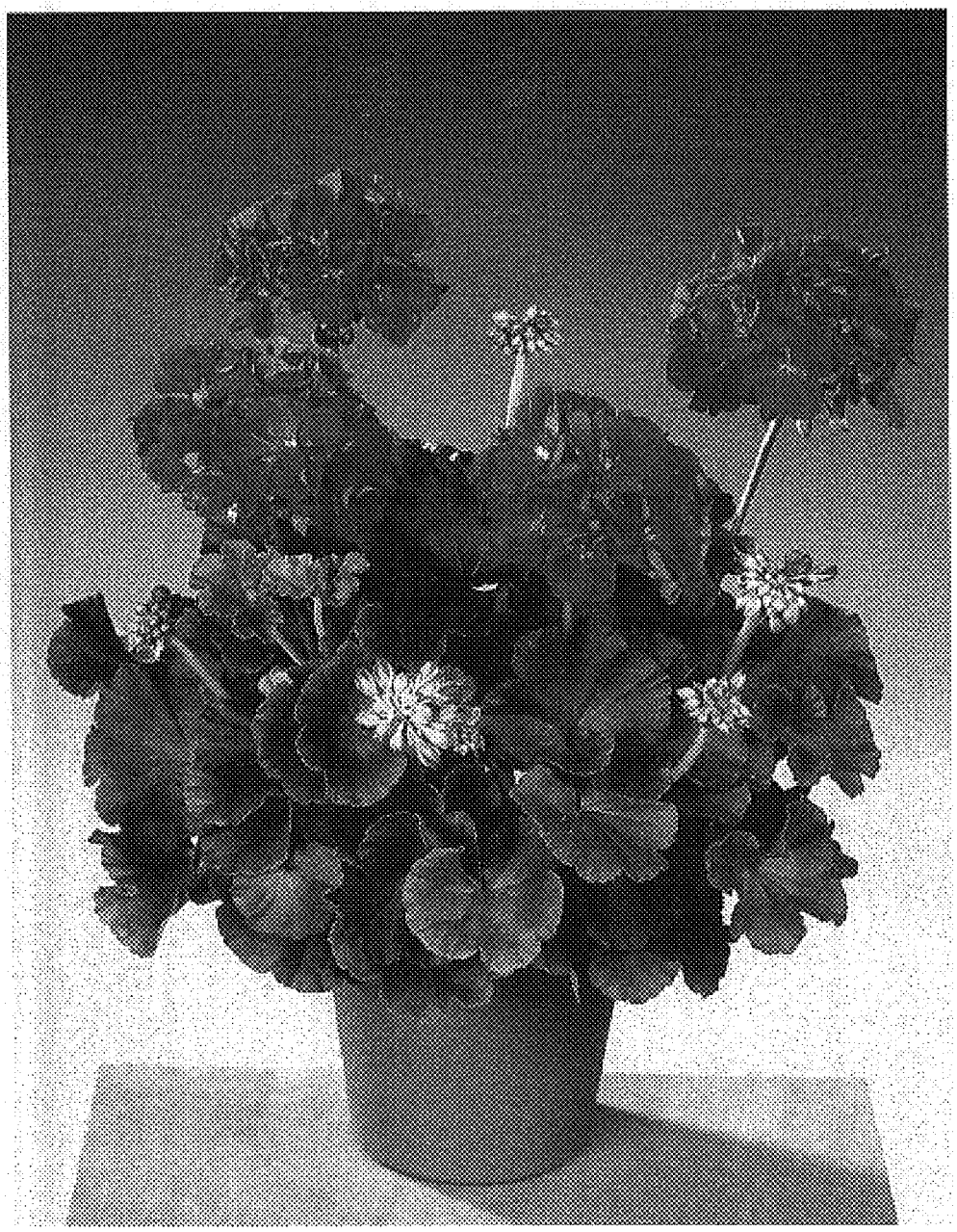

* * * * *